United States Patent
Johnson et al.

(10) Patent No.: US 8,613,723 B2
(45) Date of Patent: Dec. 24, 2013

(54) MULTI LUMEN HEAT EXCHANGER

(75) Inventors: Michael Johnson, Whitman, MA (US); Gregory Hughes, Hanover, MA (US)

(73) Assignee: Smiths Medical ASD, Inc., Rockland, MA (US)

(*) Notice: Subject to any disclaimer, the term of this patent is extended or adjusted under 35 U.S.C. 154(b) by 995 days.

(21) Appl. No.: 12/458,081

(22) Filed: Jun. 30, 2009

(65) Prior Publication Data

US 2010/0006263 A1   Jan. 14, 2010

Related U.S. Application Data

(60) Provisional application No. 61/129,681, filed on Jul. 11, 2008.

(51) Int. Cl.
| | | |
|---|---|---|
| *A61F 7/12* | (2006.01) | |
| *A61F 7/00* | (2006.01) | |
| *A61M 25/16* | (2006.01) | |
| *A61M 25/00* | (2006.01) | |
| *A61M 39/00* | (2006.01) | |
| *A61M 39/10* | (2006.01) | |

(52) U.S. Cl.
USPC ................. 604/113; 604/291; 604/533

(58) Field of Classification Search
USPC .......... 604/113–114, 291, 533, 6.13, 22, 905, 604/595
See application file for complete search history.

(56) References Cited

U.S. PATENT DOCUMENTS

| | | | |
|---|---|---|---|
| 4,623,333 A | 11/1986 | Fried | |
| 4,878,537 A | 11/1989 | Verkaart | |
| 5,097,898 A | 3/1992 | Verkaart | |
| 5,417,274 A | 5/1995 | Verkaart | |
| 5,514,095 A * | 5/1996 | Brightbill et al. ............ | 604/113 |
| 6,623,516 B2 | 9/2003 | Saab | |
| 6,641,556 B1 | 11/2003 | Shigezawa | |
| RE39,075 E | 4/2006 | Verkaart | |

FOREIGN PATENT DOCUMENTS

| | | |
|---|---|---|
| JP | 2003-339866 | 12/2003 |
| JP | 2006-212075 | 8/2006 |

* cited by examiner

*Primary Examiner* — Nicholas Lucchesi
*Assistant Examiner* — Rebecca E Eisenberg
(74) *Attorney, Agent, or Firm* — Louis Woo

(57) ABSTRACT

A heat exchanger has a multi-lumen tubing having one end connected to a supply fitting and another end connected to a return fitting. The tubing has a central lumen, a middle lumen that surrounds the central lumen and an outer lumen that surrounds the middle lumen. When infusate traverses along the heat exchanger, it is heated by the heating fluid that flows along the central lumen, and also by the rerouted heating fluid that flows along the outer lumen of the tubing. The heat exchanger is fluidly coupled to a heater by its inlet and outlet so that the temperature of the heating fluid for warming the infusate is maintained at a predetermined temperature.

20 Claims, 5 Drawing Sheets

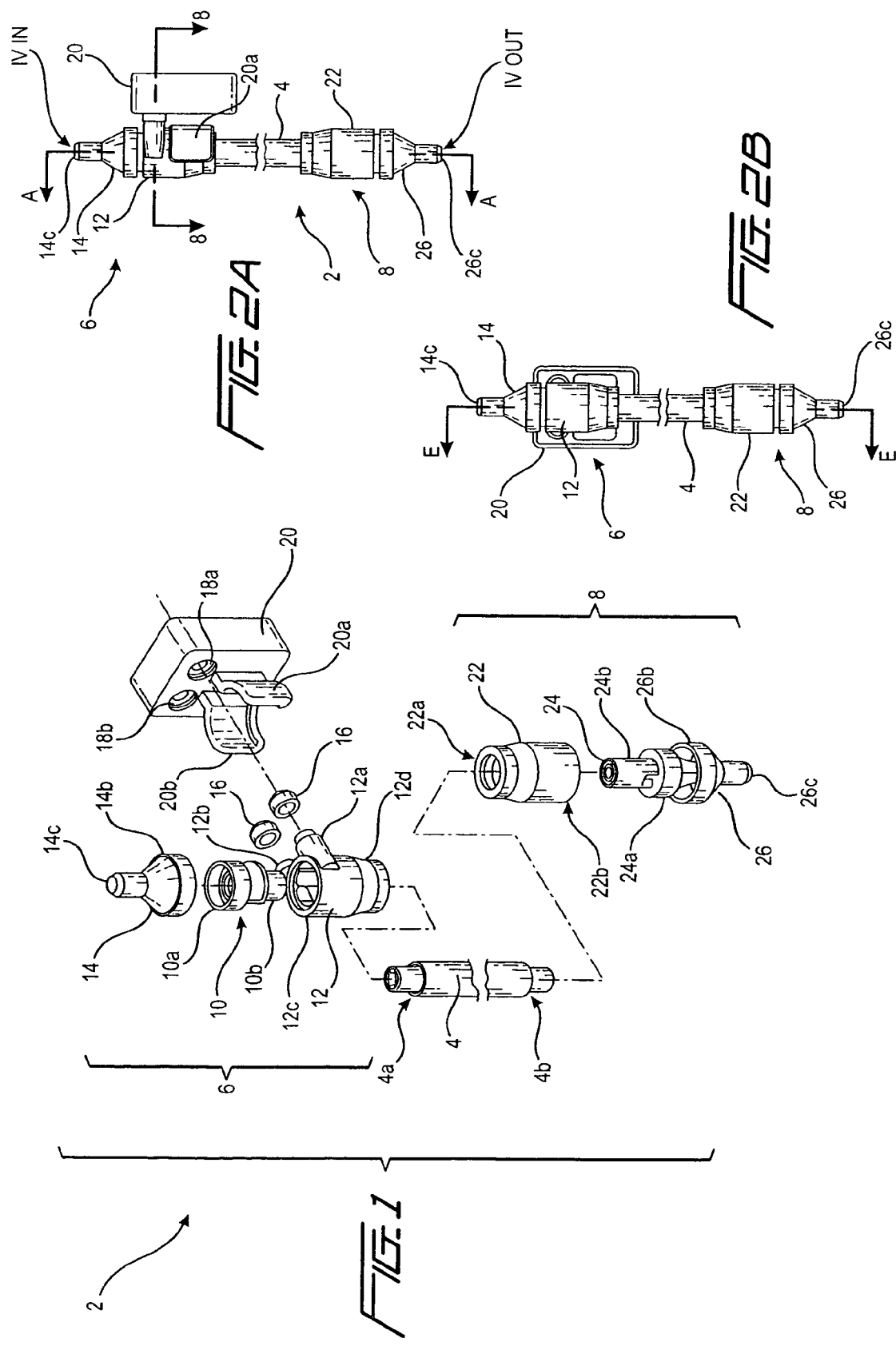

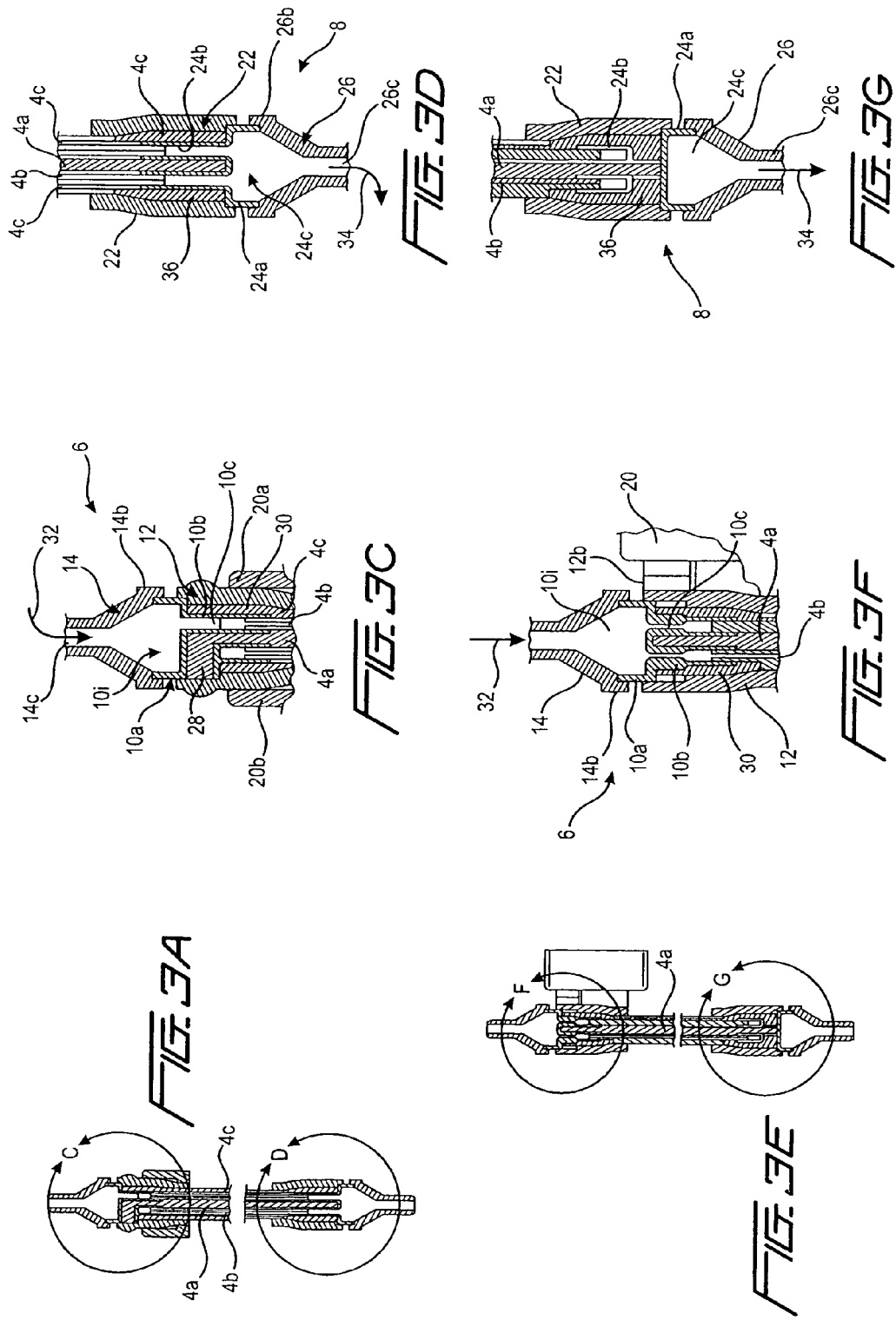

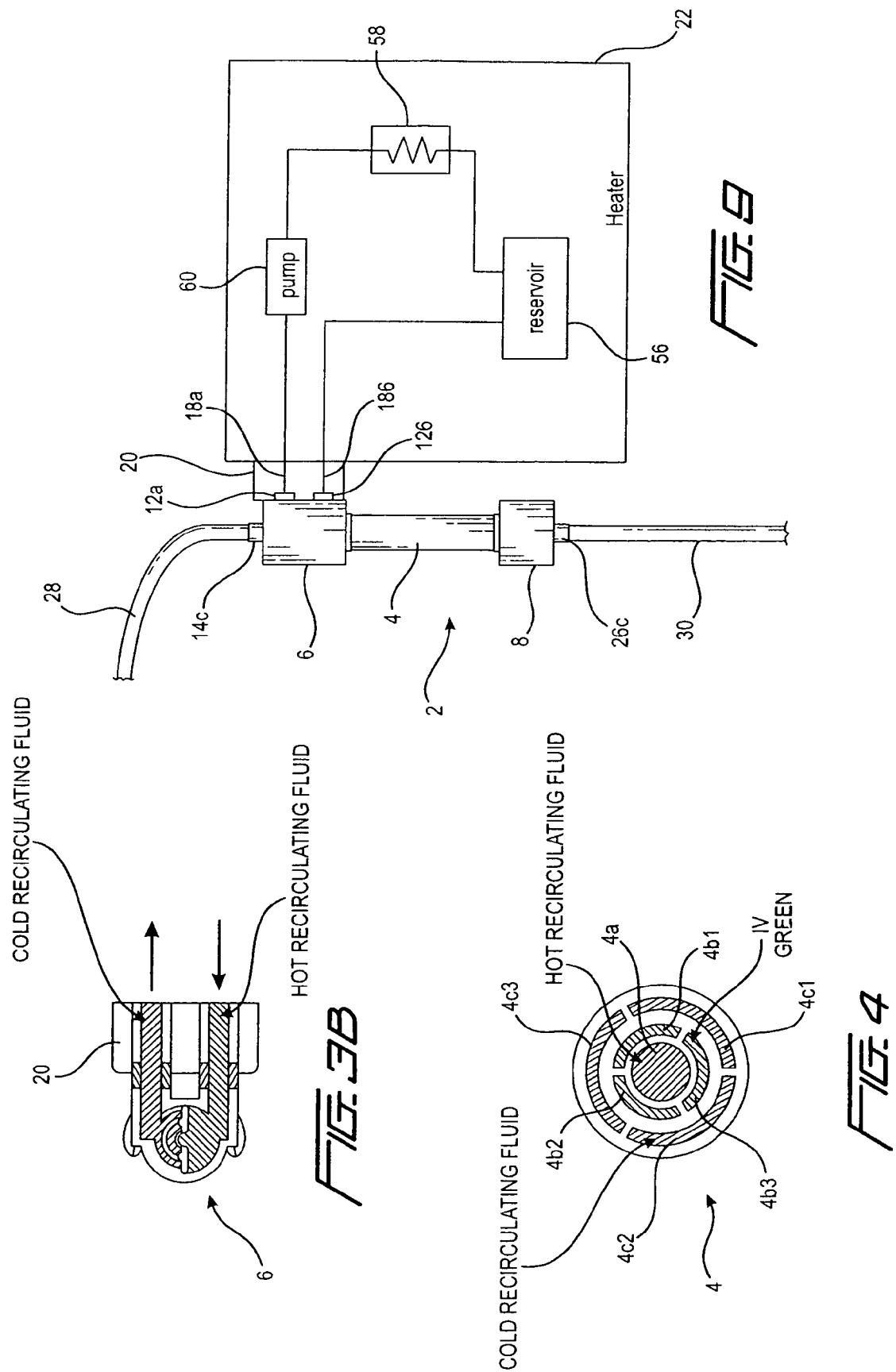

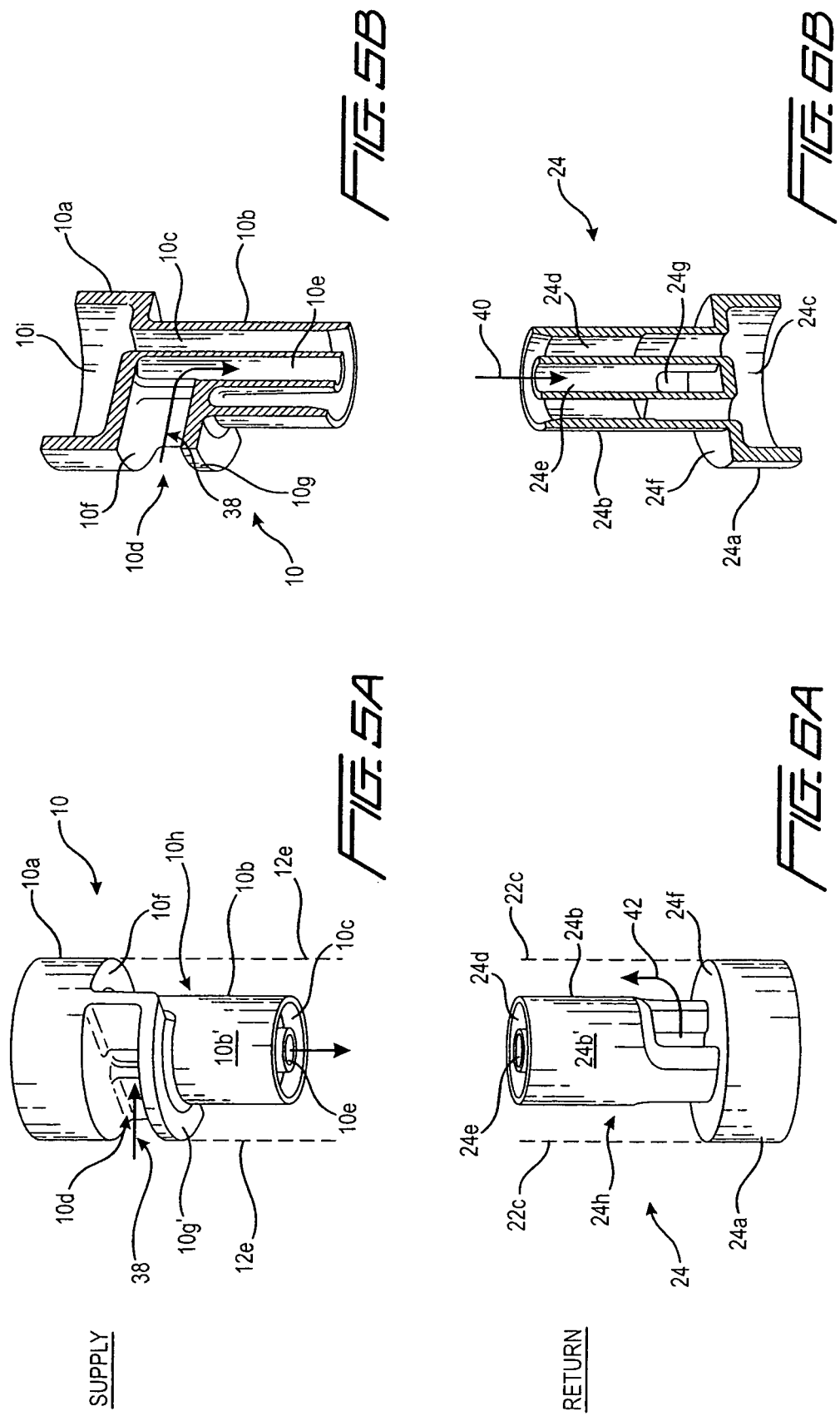

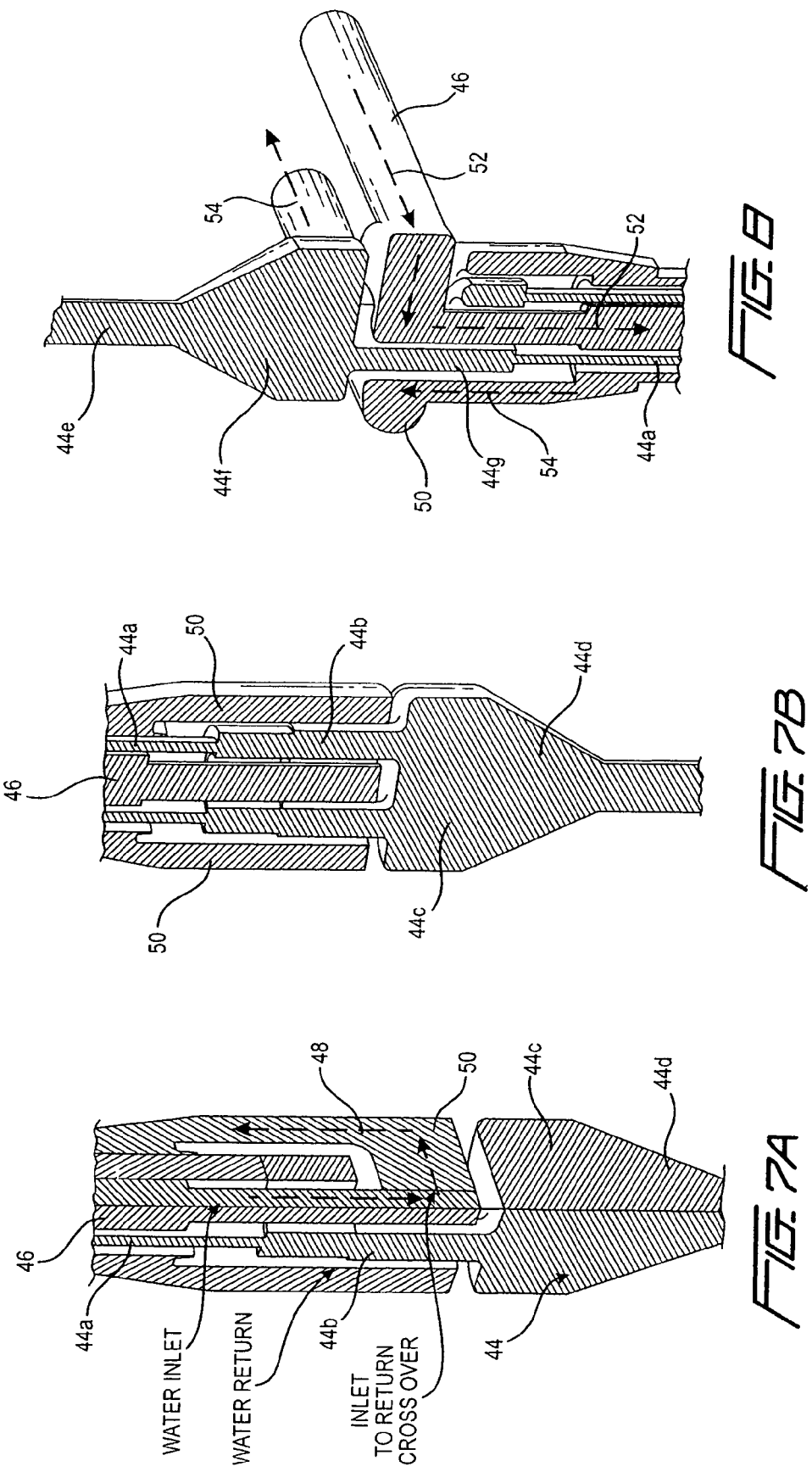

MULTI LUMEN HEAT EXCHANGER

FIELD OF THE INVENTION

The present invention relates to the art of heat exchangers, and particularly to heat exchangers that are used for heating physiological infusate or solutions.

BACKGROUND OF THE INVENTION

Heat exchangers for warming physiological solutions are known. One such heat exchanger is disclosed in U.S. Pat. Nos. 4,759,749 and 4,878,537, both assigned to the assignee of the instant invention. The heat exchanger disclosed in the '749 and '537 patents has an outer conduit covering an inner conduit that is made of aluminum. End caps seal the outer conduit. A through channel is provided by the inner conduit and another flow channel is provided between the outer wall of the inner conduit and the inner wall of the outer conduit. The outer wall of the inner conduit has a spiral configuration so that the infusate that is to be heated would follow the spiral path established between the outer wall of the inner conduit and the inner wall of the outer conduit. The infusate is therefore heated by convection from the wall of the inner conduit. This heat exchanger works well. However, due to the fact that the inner conduit is made of aluminum, the cost of manufacturing the heat exchanger is relatively high. Moreover, a multi-step manufacturing process is required to effect a spiraled path at the outer wall of the inner conduit and the fitting of the inner conduit to the outer conduit, and to ensure that there is a flow channel established between the outer spiraled wall of the inner conduit and the inner wall of the outer conduit. Furthermore, given that only the inner conduit is heated by the heated water from the heater, the infusate is only convectively heated by the heat at the outer wall of the inner conduit, while at the same time heat loss occurs due to the infusate contacting the inner wall of the outer conduit which is exposed to atmosphere.

SUMMARY OF THE PRESENT INVENTION

The present invention heat exchanger has a one piece tubing that is configured to have a central lumen, a middle lumen that surrounds the central lumen, and an outer lumen that surrounds the middle lumen. The tubing is made of medical grade plastics material, such as for example PVC, urethane and Pebax, and can be manufactured by a conventional extrusion method whereby the tubing is extruded from a mold to include the central and concentric middle and outer lumens. A supply fitting is connected to one end of the tubing. This supply fitting has a proximal port, an inlet and an outlet, and is configured to connect the proximal port to the middle lumen, the inlet to the central lumen and the outlet to the outer lumen. A return fitting is connected to the other end of the tubing. The return fitting has a distal port and an internal orifice that establishes a through passageway between the central lumen and the outer lumen of the tubing. The return fitting is further configured to connect the middle lumen to the distal port, so that a through passage extends from the proximal port at the supply fitting to the distal port at the return tubing.

The proximal port is connected to an infusate line so that infusate or physiological solution may be input to the heat exchanger. The inlet and the outlet of the supply fitting are mated to an output port and input port, respectively, of a heater device that is adaptable to heat a fluid to a predetermined temperature and output the temperature regulated fluid through its output port to the inlet of the heat exchanger, and to receive from the outlet of the heat exchanger, via its inlet port, the fluid that has circulated through the heat exchanger for reheating. The distal port at the return fitting outputs the infusate to a patient or a patient line.

With the construction of the heat exchanger of the instant invention, a heated or heating fluid, such as for example heated water, is provided from the heater device to the supply fitting of the heat exchanger. This heated fluid is then fed by the supply fitting to the central lumen of the tubing where, by means of the internal orifice at its distal end, which is at the return fitting, the heated fluid is routed to the outer lumen of the tubing. As the heated fluid from the heater traverses through the central lumen, the central lumen is heated; and as the heated fluid is rerouted to the outer lumen, the outer lumen is heated, albeit the temperature of the heated fluid returned by the outer lumen to the supply fitting is at a lower temperature, due to heat loss, than that fed by the heater device to the supply fitting. The cooler heating fluid is returned to the heater device where it is once more heated to the predetermined temperature and re-circulated back to the heater exchanger. In the meantime, the infusate input to the heat exchanger at the proximal port, which is traversing through the heat exchanger by way of the latter's middle lumen, is heated convectively by the heat being conducted from both the central lumen and the outer lumen. In other words, the infusate that flows through the middle lumen of the heat exchanger tubing is enveloped by heat from the heating fluid with no heat loss to the ambient environment. The infusate thus warmed by the heated fluid is output from the distal port of the returned fitting.

The present invention therefore is directed to a heat exchanger that comprises a tubing having a central lumen, a middle lumen surrounding the central lumen and an outer lumen surrounding the middle lumen. The heat exchanger further includes a supply fitting connected to one end of the tubing. The supply fitting has a proximal port, an inlet and an outlet, and is configured to connect the proximal port to the middle lumen, the inlet to the central lumen and the outlet to the outer lumen. Also included in the heat exchanger is a return fitting connected to the other end of the tubing. The return fitting has a distal port and an internal orifice, and is configured to connect the middle lumen of the tubing to the distal port so that a through path is established between the proximal port of the supply fitting and the distal port of the return fitting. The return fitting further is configured to establish a through passage between the central lumen and the outer lumen via the internal orifice, such that a fluid input to the inlet at the supply fitting would flow from the supply fitting to the central lumen and then be rerouted to the outer lumen and thereafter the outlet at the supply fitting.

The present invention is further directed to a heat exchanger that comprises a tubing having one end fixedly connected to its supply fitting and an other end fixedly connected to a return fitting. The tubing has a central lumen, a middle lumen surrounding the central lumen and an outer lumen surrounding the middle lumen. The supply fitting has an inlet in fluid communication with the central lumen and an outlet in fluid communication with the outer lumen. The return fitting is configured to have an internal orifice for establishing a fluid communication passage between the central lumen and the outer lumen. A proximal port is provided at the supply fitting and a distal port is provided at the return fitting. The proximal and distal ports are connected by the middle lumen, with the proximal port connectable to an infusate line and the distal port connectable to a patient line. The inlet and the outlet at the supply fitting are mateable to an output port and an input port, respectively, of a heater device so that a heated fluid may be output from the heater device to circulate from the central lumen to the outer lumen and then back to the heater device via the input port, so that an infusate that flows through the proximal port, the middle lumen and the distal port is heated by the heated fluid that circulates through the central and outer lumens.

The instant invention is further related to a heat exchanger tube that comprises an elongate tube extruded from a plastics material to have a central lumen, a middle lumen surrounding the central lumen and an outer lumen surrounding the middle lumen. Each of the lumens has a plurality of sections separated by the plastics material, with each of the sections of each of the lumens extending along the length of each of the lumens. One end of the tube is fixedly connected to a supply fitting and the other end of the tube is fixedly connected to a return fitting. A passageway is provided between the central and outer lumen at the return fitting to enable a first fluid to circulate between the central and outer lumens.

BRIEF DESCRIPTION OF THE FIGURES

The present invention will become more apparent and the invention itself will be best understood by reference to the following description of the invention taken in conjunction with the following drawings, wherein:

FIG. 1 is a disassembled view of the various components of the instant invention heat exchanger, shown relative to a mount to which the supply fitting of the heat exchanger is coupled;

FIGS. 2A and 2B are side views of the assembled FIG. 1 heat exchanger coupled to the mount of a heater device;

FIG. 3A is a sectional view along section A-A of FIG. 2A;

FIG. 3B is a cross-sectional view along section B-B of FIG. 2A;

FIG. 3C is an enlarged view of detail C shown in FIG. 3A;

FIG. 3D is an enlarged view of detail D shown in FIG. 3A;

FIG. 3E is a cross-sectional along section E-E shown in FIG. 2B;

FIG. 3F is an enlarged view of detail F of FIG. 3E;

FIG. 3G is an enlarged view of detail G shown in FIG. 3E;

FIG. 4 is a cross-sectional view of the tubing of the instant invention heat exchanger;

FIG. 5A is a perspective view of the core of the supply fitting of the heat exchanger of the instant invention;

FIG. 5B is a cross-sectional view of the core of the supply fitting;

FIG. 6A is a perspective view of the core of the return fitting of the inventive heat exchanger;

FIG. 6B is a cross-sectional view of the core of the return fitting;

FIG. 7A shows in perspective view the fluid paths at the distal end of the heat exchanger sans the physical components;

FIG. 7B is a cross-sectional view of the fluid paths of FIG. 7A;

FIG. 8 is a view showing the fluid paths of the various fluids at the proximal end of the heat exchanger sans the physical components; and FIG. 9 is a simplified schematic illustrating the heat exchanger of the instant invention coupled to a heater device.

DETAILED DESCRIPTION OF THE INVENTION

With reference to FIG. 1, the heat exchanger 2 of the instant invention is shown to include a tubing 4, a supply fitting 6 and a return fitting 8. Supply fitting 6 is shown to include a core 10, a housing 12 to which the core is fitted, and a cap 14 that fixedly attaches to the top end of core 10 for providing a sealed environment for the supply fitting. As shown, housing 12 has two hollow arms 12a and 12b each fitted with a corresponding gasket 16, so that arms 12a and 12b may be mated to ports 18a and 18b, respectively, of a mount 20 that is a part of a heater device 22, per shown in FIG. 9. The main part of core 10 is fitted to the inside of housing 12, and the base 14b of cap 14 is fixedly secured, for example by bonding, to the proximal end 10a of core 10, per shown in FIG. 3A for example. The distal end 12d of housing 12 is connected to the distal end 4a of tubing 4.

Return fitting 8 has a housing 22, a core 24 fitted in the housing and a cap 26. Housing 22 has a proximal end 22a that fixedly attaches to distal end 4b of tubing 4. Core 24 is fitted inside housing 22, and the base 26b of cap 26 is securely bonded to a base 24a of core 24 so as to form a sealed environment for return fitting 8. Given that tubing 4 is sealingly attached to supply fitting 6 per its proximal end 4a and to return fitting 24 per its distal end 4b, by capping its proximal port 14c at cap of 14 and the distal port 26c at cap 16, the heat exchanger 2 is sealed against the environment and remains sterile before use.

FIGS. 2A and 2B show the coupling of heat exchanger 2 to mount 20 of a heater device. As shown, cap 14 of supply fitting 6 has a bore for its distal port 14c. It is at this port that an infusate line 28, shown in FIG. 9, is connected to enable an infusate, such as for example an intravenous (IV) fluid or other physiological fluids, to be introduced to the heat exchanger 2. The infusate is conveyed along the heat exchanger 2 and exits at a bore that forms the distal port 26c at cap 26 of the return fitting 8. A patient line, such as 30 shown in FIG. 9, may be connected to distal port 26c for conveying the infusate to a patient.

With reference to the cross-sectional view of section A-A in FIG. 3A and the cross-sectional view of FIG. 4, tubing 4 is shown to have a central lumen 4a, a middle lumen 4b that surrounds the central lumen 4a, and an outer lumen 4c that surrounds the middle lumen 4b. The diameter of the central lumen 4a is much larger than the respective widths of the middle and outer lumens. Note that the concentric middle lumen 4b and outer lumen 4c each comprise a plurality of sections, for example 4b1, 4b2 and 4b3 for the middle lumen 4b, and 4c1, 4c2 and 4c3 for the outer lumen 4c. The various sections of lumens 4b and 4c extend along the length of each of the lumens. The multiple sections of lumens 4b and 4c are separated by the plastics material in a spoke wheel fashion, which is effected when tubing 4 is extruded from a medical plastics material such as PVC, urethane and Pebax by a conventional extrusion method. To enable tubing 4 to be fixedly connected to housing 12 of supply fitting 6 and housing 22 of return fitting 8 in a manner that allows the warming of the infusate, the central portion of tubing 4 is extended at its proximal end 4a and its distal end 4b, per shown in FIG. 1 and the cross-sectional views of FIGS. 3A and 3E.

With reference to FIGS. 3C and 3F illustrating the enlarged details C and F, respectively, the proximal end of the heat exchanger is shown to include cap 14, housing 12 and core 10 of supply fitting 6. Base 10a of core 10 is shown to form an upside down well 10i that is fixedly attached to base 14b of cap 14. Well 10i of core 10 extends to a passageway 10c that is connected to the middle lumen 4b of tubing 4. The central lumen 4a of tubing 4 is shown to be connected to core 10 and exits to a space 28, which leads to the inlet of supply fitting 6 represented by the hollow arm 12a shown in FIG. 1. Outer lumen 4c is shown to extend into a passageway 30 defined by the external wall of a tubular extension 10b of core 10 and the inside wall of housing 12. Supply fitting 6 is also shown to be grasped by arms 20a and 20b of mount 20 in FIG. 3C.

The cross-sectional view of enlarged detail F of FIG. 3F shows the mating of outlet 12b of supply fitting 6 to mount 20. As shown, the infusate is fed through bore 14c of cap 14 into the cavity formed by well 10i, per directional arrow 32. The infusate is then directed to the passageway 10c at tubular extension 10b of core 10, and from there to the middle lumen 4b.

With reference to FIGS. 3D and 3G, which are the enlarged details D and G, respectively, of FIGS. 3A and 3E, the distal end of the heat exchanger where the return fitting 8 is connected to tubing 4 is illustrated. As shown, base 24a of core 24 is fixedly bonded to base 26b of cap 26. The well area formed by base 24a of core 24 is designated 24c. It is there that the infusate input from proximal port 14c of cap 14 at supply fitting 6 is fed, by means of middle lumen 4b. The infusate collected at cap 24b is output from distal port 26c to the patient line 30 (FIG. 9), per directional arrow 34.

As further shown in FIG. 3D, and also FIGS. 8a and 8b, between the inner wall of housing 22 and the outer wall of tubular extension 24b there is a circular space 36 that connects to outer lumen 4c of tubing 4. This circular space is where the heated fluid that flows through central lumen 4a is being rerouted to outer lumen 4c for return to the supply fitting, and from there returned to the heater device for reheating. The space at supply fitting 6 to which the cooler heating fluid is returned had previously been designated as space 30. Thus, the hot recirculating fluid, i.e., the heated water for example, is fed by heater device 22 from its output port 18a to supply fitting 6, which routes it to central lumen 4a of tubing 4. The heated fluid is then returned to heater device 22 by means of outer lumen 4c.

A cross-sectional view illustrating the flow of the heated fluid from the heater device to the heat exchanger, and the return of the heated fluid back to the heater device at supply fitting 6 is shown in FIG. 3B. The feeding of the heated fluid from the heater device to the supply fitting, and the routing of the heated fluid and the infusate to tubing 4 are best discussed with reference to core 10 for the supply fitting shown in FIGS. 5A and 5B.

As shown, core 10 for supply fitting 6 has a base portion 10a and a tubular extension 10b. Base 10a has a well area 10i that, together with cap 14 shown in FIG. 3C, provide a cavity whereto the infusate from an infusate line is fed. Well 10i extends to a passageway 10c at tubular extension 10b. Passageway 10c in turn is connected to middle lumen 4b, so that the infusate can be conveyed from proximal port 14c, shown in FIG. 3c, to middle lumen 4b.

Core 10 also has a space 10d that forms a part of the inlet that connects to output port 18a of mount 20 of the heater device. Space 10d is aligned with hollow arm 12a of housing 12, when core 10 is fitted within housing 12. Thus, the heated fluid output from output port 18a of the heater device is fed through inlet 12a into space 10d, and from there flows to a passageway 10e that is connected to central lumen 4a of tubing 4. The flow of the heated fluid from the heater device is shown per directional arrow 38. Space 10d is defined by the back wall 10f of base 10a and a flange 10g, and of course also the inside wall of housing 12 when core 10 is fitted therein.

Core 10 for supply fitting 6 further has a space 10h, when core 10 is fitted within housing 12, that is defined by the back wall 10f of base 10d, the underside 10g' of flange 10g, the outer wall of tubular extension 10b, designated 10b', and the inside wall, designated by the dotted lines 12e in FIG. 5a, of housing 12. This space 10h is communicatively connected to outer lumen 4c of tubing 4 so that it in effect, along with hollow arm 12b, provide the outlet for supply fitting 6 to mate to inlet port 18b of mount 20. It is therefore through this outlet that the heated fluid, now having been cooled due to heat dissipation as it flows through the heat exchanger, is returned to heater device 22 for reheating, and subsequent re-circulation through the heat exchanger.

With reference to FIGS. 6A and 6B, core 24 for the return fitting has a base 24a and a tubular extension 24b. As was the case with supply fitting core 10, base 24a of return fitting core 24 provides a well area 24c that is fixedly coupled to base 26b of cap 26, which is connected to patient line 30 for outputting the infusate to the patient. As shown, cavity 24c extends into a circumferential passageway 24d, that in turn is connected to the middle lumen 4b of tubing 4. A fluid communication path is thereby established between cavity 24c and passageway 24d of return fitting 8, middle lumen 4b, and passageway 10c and cavity 10i of supply fitting core 10.

There is formed at return fitting core 24a central passage 24e that ends at the back wall 24f of base 24a. An internal orifice 24g is formed at the lowermost portion of passageway 24e that connects passageway 24e to a space 24h that is defined by the back wall 24f of base 24a, the outside wall 24b' of tubular extension 24b and the inside wall of housing 22, designated by the dotted line 22c in FIG. 6A. Space 24h in turn is connected to outside lumen 4c, so that a through passage extends from space 24h to lumen 4c, and from there to defined space 10h at supply fitting 6, per shown in FIG. 5A, so that the heated fluid from central lumen 4a that flows through passage 24e, per shown by directional arrow 40, would pass through orifice 24g, and be rerouted into defined space 24h, per shown by directional arrow 42. The rerouted heated fluid is then directed to outer lumen 4c of tubing 4, and from there to defined space 10h of supply fitting 6 for return to the input port 18b of the heater device.

The respective flows of the infusate and the heated recirculating fluid are shown in FIGS. 7A, 7B and 8. For the sake of clarity, only the fluids are shown.

With reference to the distal end of the heat exchanger shown in FIGS. 7A and 7B, note that the infusate (IV) 44 flows from the middle lumen, designated 44a, to the tubular extension of the return fitting, identified as 44b, and from there to the base of the return fitting, designated 44c. The infusate next is output to the cavity formed by the return fitting cap and the base of the return fitting core, designated 44d, and then out to the patient line.

In the meanwhile, the heated fluid, for example heated water, flows through the central lumen, designated 46 in FIGS. 7A and 7B. As best shown in FIG. 7A, the hot fluid traverses down the central lumen. Due to internal orifice 24g provided at return fitting core 24 (FIGS. 6A and 6B) that creates a passageway between the central lumen and the outer lumen, the hot fluid is rerouted, per indicated by directional arrow 48, from the central lumen to the outer lumen. By the time that the heated fluid gets to the distal end of the heat exchanger, it has lost a measurable amount of heat due to heat dissipation. Therefore, the return fluid, designated 50, has a cooler temperature than heated fluid 46 flowing along the central lumen of the heat exchanger. Nonetheless, there continues to be heat in the cooler heating fluid as it traverses to the proximal end of the heat exchanger where the supply fitting is.

With reference to FIG. 8, it can be seen that hot fluid 46 from the heater is fed to the heat exchanger at the latter's inlet. Being guided by space 10d of the supply fitting (FIGS. 5A and 5B), hot fluid 46 is fed to the tubular extension of the supply fitting core, and then the central lumen of the tubing, per shown by the directional arrow 52. The being returned cooler heating fluid 50 is shown to flow along the outer lumen of the tubing and also space 10h defined by the supply fitting core and the supply fitting housing, so that the cooler heating fluid is returned to the outlet of the heat exchanger and the input port of the heater device, per shown by the direction arrow 54. In the meanwhile, infusate 44 is fed from an infusate line to the proximal port of the supply fitting, designated 44e, flows into the cavity defined by the supply fitting cap and the supply fitting core base, designated 44f, and from there through the tubular extension of the supply fitting core, designated 44g, and finally to the central lumen, previously designated 44a in FIGS. 7A and 7B.

As the middle lumen of the heat exchanger tube concentrically bounds the central lumen and is in turn concentrically bounded by the outer lumen, when the infusate flows through the central lumen, heat exchange is provided thereto from both directions at both its inside and outside perimeters due to the recirculating heating fluid flowing along the central lumen and the outer lumen. The effective heat exchange to the infusate by the instant invention tubing is maximized due to the narrow annular shape of the central lumen, which provides a large effective perimeter for heat exchange from the recirculating fluid to take place. Further, the temperature gradient of the hot recirculated fluid in the central lumen radiates outwards toward the infusate for maximally warming the infusate. The heating of the heat exchanger of the instant invention is therefore quite efficient in that there is no direct heat loss by the hot fluid flowing through the central lumen, as it is surrounded by the infusate flowing through the central lumen.

FIG. 9 shows the coupling of the heat exchanger to a heater device 22. As shown, outlet 12b and inlet 12a of supply fitting 6 are mated to inlet port 18b and output port 18a, respectively, of mount 20 of heater device 22. The heater device 22 may be a Level 1 H-1200 Fast Flow Fluid Warmer. The returned fluid from the heat exchanger is first routed to a reservoir 56, and from there to a heater 58. A pump 60 pumps the heated fluid to output port 18a, and from there to inlet 12a of the heat exchanger for circulation as discussed above. Pump 60, instead of being placed at the output line of the heater device, may also be placed at the input line to enhance the inflow of the cooler heating fluid being returned to heater device 22.

An infusate line 28 is connected to proximal port 14c of supply fitting 6, while a patient line 30 is connected to distal port 26c at return fitting 8 of the heat exchanger. As discussed above, the infusate, as it flows from the proximal end to the distal end of the heat exchanger via the central lumen, is heated both by the central lumen through which the hot fluid flows and the outer lumen through which the now cooler heating fluid is being returned to the heater device. As the heating fluid is continuously circulated through the heat exchanger, the temperature of the fluid is kept to a predetermined temperature so that the amount of heat for warming the infusate or other physiological fluids fed to the heat exchanger can be readily regulated.

Inasmuch as the present invention is subject to many variations, modifications and changes in detail, it is intended that all matters described throughout this specification and shown in the accompanying drawings be interpreted as illustrative only and not in a limiting sense. Accordingly, it is intended that the invention be limited only the spirit and scope of the hereto appended claims.

The invention claimed is:
1. A heat exchanger, comprising:
a tubing having a central lumen, a middle lumen surrounding said central lumen and an outer lumen surrounding said middle lumen;
a supply fitting connected to one end of said tubing, said supply fitting having a proximal port, an inlet and an outlet, said supply fitting configured to connect said proximal port to said middle lumen, said inlet to said central lumen and said outlet to said outer lumen;
a return fitting connected to other end of said tubing, said return fitting having a distal port and an internal orifice, said return fitting configured to connect said middle lumen to said distal port so that a through passage is established between said proximal port and said distal port, said return fitting further configured to establish a passage between said central lumen and said outer lumen via said internal orifice;
wherein a fluid input to said inlet at said supply fitting flows from said supply fitting to said central lumen and is rerouted through said internal orifice to said outer lumen for circulation to said outlet at said supply fitting.

2. Heat exchanger of claim 1, wherein the fluid input to said inlet is heated water output from a heater device, said inlet matable to an output port at said heater device, the heated water fed to said inlet from said output port.

3. Heat exchanger of claim 1, wherein the fluid being circulated to said outlet is heated water, the temperature of the water returned to said outlet being cooler than the temperature of the water input to said inlet, the cooler water output from said outlet to an input port of a heater device mated to said outlet, the cooler water being reheated in said heater device to a predetermined temperature.

4. Heat exchanger of claim 1, wherein said inlet and outlet are mated to an input port and an output port, respectively, of a mount at a heater device when said supply fitting is removably coupled to said mount.

5. Heat exchanger of claim 1, wherein said proximal port is connected to an infusate line so that an infusate enters said heat exchanger through said proximal port, flows through said middle lumen and outputs from said distal port at said return fitting.

6. Heat exchanger of claim 4, wherein the fluid input to said inlet from said heater device is heated water, the heated water circulating in said heat exchanger through said central lumen and said outer lumen for warming an infusate passing through said middle lumen.

7. Heat exchanger of claim 1, wherein said tubing is extrusion molded from a plastics material.

8. A heat exchanger, comprising: a tubing having one end fixedly connected to a supply fitting and other end fixedly connected to a return fitting; said tubing having a central lumen, a middle lumen surrounding said central lumen and an outer lumen surrounding said middle lumen; said supply fitting having an inlet in fluid communication with said central lumen and an outlet in fluid communication with said outer lumen; said return fitting configured to have an internal orifice for establishing a fluid communication passage between said central lumen and said outer lumen; a proximal port provided at said supply fitting and a distal port provided at said return fitting, said proximal and distal ports connected by said middle lumen, said proximal port connectable to an infusate line and said distal port connectable to a patient line; said inlet and outlet matable to an output port and an input port, respectively, of a heater device so that a heated fluid may be output from said heater device to circulate from said central lumen to said outer lumen and then back to said heater device via said input port; wherein an infusate flowing from said proximal port through said middle lumen and out of said distal port is heated by the heated fluid circulating through said central and outer lumens.

9. Heat exchanger of claim 8, wherein the fluid being circulated is heated water, the temperature of the water returned to said outlet being cooler than the temperature of the water input to said inlet, the cooler water output from said outlet returns to said heater device via said input port for reheating and recirculation to said central lumen.

10. Heat exchanger of claim 8, wherein said supply fitting comprises a core having a base with a tubular extension, a well formed in said base and extending into a first passage in said tubular extension that connects to said middle lumen of said tubing, a space defined by a flange and the back wall of said well at said extension for forming a part of said inlet, said space extending to a central passageway at said tubular extension that connects to said central lumen of said tubing, and a void defined between said flange and the back wall of said well adjacent to said space for forming a part of said outlet.

11. Heat exchanger of claim 10, wherein said supply fitting further comprises a housing whereinto said core fits, said housing having first and second hollow arms that form the inlet and outlet, respectively, that correspondingly mate to the output port and input port of said heater device, an inner wall of said housing and the outer wall of said extension forming an outer passageway that connects to said outer lumen through which the heated fluid may be returned to said heater device.

12. Heat exchanger of claim 10, wherein said supply fitting further comprises a cap having a bore that forms said proximal port, said cap secured to said core for forming a sealed cavity with said well, the infusate flowing from the infusate line through said bore into said well and from there to said first passage and said middle lumen.

13. Heat exchanger of claim 8, wherein said return fitting comprises a core having a base with a tubular extension, a well formed in said base and extending to an outer passage in said tubular extension, a central passageway connected to said central lumen ended at the back wall of said well having at least a portion surrounded by said outer passage, said internal orifice formed at a portion of said passageway close to the back wall of said well for establishing the fluid communication passage between said central lumen and said outer lumen.

14. Heat exchanger of claim 13, wherein said return fitting further comprises a housing whereinto said core fits, an inner wall of said housing and the outer wall of said tubular extension forming an outer passageway that connects to said outer lumen of said tubing for the heated fluid passing through said internal orifice from said central passageway to be returned to said heater device.

15. Heat exchanger of claim 13, wherein said return fitting further comprises a cap having a bore that forms said distal port, said cap secured to said core for forming a sealed cavity with said well, the infusate flowing from said middle lumen of said tubing to said cavity and through said bore to the patient line.

16. A heat exchanger tubing comprising: an elongate tube extruded from a plastics material to have a central lumen, a middle lumen surrounding said central lumen and an outer lumen surrounding said middle lumen, each of said middle and outer lumens having a plurality of sections separated by the plastics material, each of said sections of each of said middle and outer lumens extending along the length of each of said lumens, one end of said tube fixedly connected to a supply fitting and other end of said tube fixedly connected to a return fitting, a through passage provided between said central and outer lumens at said return fitting to enable a first fluid to circulate between said central and outer lumens.

17. Heat exchanger tubing of claim 16, wherein a second fluid flows from said supply fitting to said return fitting through said middle lumen.

18. Heat exchanger tubing of claim 16, wherein said first fluid is a heated fluid, said heated fluid being fed from said supply fitting to said central lumen, said heated fluid traversing along said central lumen to said return fitting, said return fitting rerouting said heated fluid via said through passage to said outer lumen for return to said supply fitting; and wherein an infusate is fed from said supply fitting to said middle lumen, said infusate traversing to said return fitting and from there out to a patient line connected to said return fitting, said infusate being heated by said heated fluid traversing in said central and outer lumens.

19. Heat exchanger tubing of claim 16, wherein said supply fitting comprises an inlet and an outlet coupled to an output port and an input port, respectively, of a heater device so that said first fluid circulating in said central and outer lumens is heated to and maintained at a predetermined temperature, said supply fitting further comprises a proximal port for accepting an infusate for passage through said middle lumen.

20. Heat exchanger tubing of claim 19, wherein said return fitting comprises an internal orifice that connects said central lumen and said outer lumen for establishing said through passageway so that said first fluid fed to said central lumen from said supply fitting is rerouted to said outer lumen for return to said supply fitting, said return fitting further comprising a distal port wherethrough the infusate can exit, the infusate being heated by said first fluid flowing through said central and outer lumens as it flows through said middle lumen.

* * * * *